United States Patent
Courvoisier

(10) Patent No.: US 9,532,856 B2
(45) Date of Patent: Jan. 3, 2017

(54) SCREW HEAD

(71) Applicant: Straumann Holding AG, Basel (CH)

(72) Inventor: Stephane Courvoisier, Colombier (CH)

(73) Assignee: Straumann Holding AG, Basel (CH)

( * ) Notice: Subject to any disclaimer, the term of this patent is extended or adjusted under 35 U.S.C. 154(b) by 0 days.

(21) Appl. No.: 14/795,249

(22) Filed: Jul. 9, 2015

(65) Prior Publication Data

US 2015/0305837 A1  Oct. 29, 2015

Related U.S. Application Data

(62) Division of application No. 13/304,552, filed on Nov. 25, 2011, now abandoned.

(30) Foreign Application Priority Data

Dec. 23, 2010 (EP) ..................................... 10016023

(51) Int. Cl.
  *A61C 8/00* (2006.01)
  *F16B 35/06* (2006.01)
  *F16B 31/00* (2006.01)

(52) U.S. Cl.
  CPC ............. *A61C 8/0074* (2013.01); *A61C 8/005* (2013.01); *A61C 8/0068* (2013.01); *F16B 35/06* (2013.01); *F16B 31/00* (2013.01)

(58) Field of Classification Search
  CPC ..... A61C 8/0074; A61C 8/005; A61C 8/0068; A61C 8/0069; F16B 35/06; F16B 31/00
  See application file for complete search history.

(56) References Cited

U.S. PATENT DOCUMENTS 4,154,138 A    5/1979  Melone
5,527,183 A *  6/1996  O'Brien ............... A61C 8/0001
                                                        433/173

(Continued)

FOREIGN PATENT DOCUMENTS

CA         1054409 A1    5/1979
DE   102008009547 A1    8/2009

(Continued)

OTHER PUBLICATIONS

European Search Report in corresponding application EP 10016023.

*Primary Examiner* — Heidi M Eide
(74) *Attorney, Agent, or Firm* — Polsinelli PC

(57) ABSTRACT

Fastening system including a screw component (10) and a seating component (20). The screw component has a shaft (12) extending along a longitudinal axis (5) and having a maximum radius $R_1$, said shaft comprising a threaded section (13), said screw component further including, at one end of the screw shaft, a head (14), the head comprising a bottom end (15) having a larger maximum radius $R_2$ than the screw shaft such that an exposed underside (18) of the screw head extends radially beyond the maximum radius of the screw shaft. The seating component includes a screw channel (21) having a planar screw seat (22) having a minimum radius $R_3$ which is equal to or greater than $R_1$. The bottom end of the screw head has an annular contact surface for abutment against said screw seat, the contact surface being formed by the distal end of at least one downwardly extending protrusion (17) on the underside of the screw head, wherein the annular contact surface has a minimum radius greater than the minimum radius of the screw seat.

13 Claims, 6 Drawing Sheets

(56) References Cited

U.S. PATENT DOCUMENTS

| | | | |
|---|---|---|---|
| 6,332,778 B1 | 12/2001 | Choung | |
| 8,226,408 B2 * | 7/2012 | Grant .................... | A61C 8/005 |
| | | | 433/173 |
| 2004/0043360 A1 * | 3/2004 | Obata .................... | A61C 8/005 |
| | | | 433/173 |
| 2005/0042573 A1 | 2/2005 | Lustig et al. | |
| 2006/0216672 A1 | 9/2006 | Dinkelacker | |
| 2008/0039837 A1 | 2/2008 | Gambale et al. | |

FOREIGN PATENT DOCUMENTS

| | | |
|---|---|---|
| EP | 1679049 A1 | 12/2006 |
| WO | 2006012273 A1 | 2/2006 |
| WO | 2008110575 A1 | 9/2008 |

* cited by examiner

SCREW HEAD

RELATED APPLICATIONS

This application is a division of U.S. Ser. No. 13/304,552, entitled Screw Head, filed 25 Nov. 2011 which claims priority to European Application No. 10 016 023.3, filed 23 Dec. 2010.

FIELD OF THE INVENTION

This invention relates to screws, particularly those used in the dental implant field to attach secondary components, such as abutments, to a dental implant.

BACKGROUND

Dental implants are used to replace individual teeth or for anchoring more complex structures, which generally replace several or even all of the teeth.

Implants are often constructed in two parts, in which case they consist of an anchoring part, often referred to in isolation as the implant, and of a separate abutment. The anchoring part is either embedded completely in the bone, that is to say to the height of the alveolar crest, or protrudes by a few millimeters from the alveolar crest into the soft tissue. The abutment is mounted on the anchoring part and extends into the oral cavity to form a support for a dental prosthesis or denture.

During the lifetime of the prosthesis, which can be over 20 years, the implant system will be subjected to large loads caused by mastication. The abutment must therefore be firmly fastened to the implant in order to prevent loosening and potential loss of the component. This can be achieved in numerous ways, for example, via compression fit or gluing. However, screw fit connections are generally preferred. By applying a sufficiently high torque during attachment a firm connection between the implant and abutment can be achieved.

In many systems therefore the implant comprises an internal threaded bore, while the abutment comprises a corresponding apical thread, thus allowing the abutment to be screwed directly into the implant.

However, this has the disadvantage that the exact angular position of the abutment relative to the implant is not known until final fixation. This can have disadvantages, particularly when the abutment is intended to support a single tooth prosthesis.

Therefore, many implant systems comprise anti-rotation means, which prevent relative rotation between the implant and abutment and which set a finite number of angular positions which the abutment can have relative to the implant.

These anti-rotation means consist of complementary non-circular symmetric portions in the implant and abutment, usually having a polygonal shape such as a hexagon or octagon.

Such systems ensure that the exact angular position of the abutment in relation to the implant is known prior to fixation and can help to prevent loosening of the abutment during the lifetime of the implant.

Of course, when such anti-rotation means are employed it is not possible to rotate the abutment relative to the implant and hence the abutment can no longer be directly screwed into the implant. Therefore a third component, often a screw known as a "basal screw", is used to connect the abutment to the implant.

When a basal screw is used the abutment typically comprises a screw channel extending through the abutment and having a screw seat. This enables the basal screw to be fed through the abutment until the screw head abuts the screw seat and for a screwdriver to be inserted into the channel to engage the screw and fasten this to the internal threaded bore of the implant, thus clamping the abutment securely to the implant.

An example of such a known implant system can be found for instance in EP1679049, in which the screw seat is conical and WO2006/012273, in which the screw seat is planar.

As well as abutments, basal screws are also used to connect other, temporary secondary components to the implant, for example, healing caps, closure screws and impression posts.

As mentioned above, it is important that the abutment in particular is firmly fastened to the implant in order to prevent loosening over the lifetime of the implant system. In the case of screw fit systems, this is achieved by tightening the screw component, whether this is a third component or the abutment itself, in order to achieve a high pre-load, or clamping force.

In order to achieve the maximum pre-load, it is desirable to tighten the screw as much as possible without reaching the yield strength of the screw. At this point, the tension within the screw body can result in plastic deformation of the threads and in some cases fracturing of the screw. This is highly undesirable as the screw must then be removed and replaced. Removal of a damaged screw is not always easy and furthermore this can result in damage to the internal threads of the implant. In some cases, the damage to the screw may not become apparent until after the final prosthesis has been fixed to the abutment, and hence the replacement of the screw can also result in the need for the creation of a new prosthesis.

Manufacturers of dental implant systems therefore set recommended maximum torque values, which ensure a high pre-loading of the screw without risking over tensioning.

However, given the natural desire to ensure a high pre-loading of the implant system, dental practitioners often apply a fastening torque significantly over the recommended value, which can lead to failure of the screw.

In order to increase the tensional strength of screws to prevent breakage in such situations, one potential solution would be to manufacture the screws from a different, stronger material. However, given the long term use of the screw within the human body any new material must undergo rigorous safety tests, and finding a new material having the necessary high strength together with the required biocompatibility is not a simple matter.

Another option would be to increase the dimensions of the screw. However, in dental implant systems space is restricted as the implant must fit within the available space within the jaw bone whilst removing as little bone mass as possible, to limit trauma at the implant site. Therefore the overall dimensions of the implant system can not be altered, and so any increase in the diameter of the screw would result in an equivalent reduction in the thickness of the implant and/or abutment. Such a modification would simply weaken the system in another area.

SUMMARY OF THE INVENTION

It is therefore an object of at least a preferred embodiment of the present invention to provide a screw component having a design which enables this to withstand a higher amount of torque without requiring a change of material or overall dimensions.

In accordance with one aspect the present invention provides a fastening system comprising a screw component and a seating component. The screw component comprises a shaft extending along a longitudinal axis and having a maximum radius $R_1$, said shaft comprising a threaded section, said screw component further comprising, at one end of the screw shaft, a head, the head comprising a bottom end having a larger maximum radius $R_2$ than the screw shaft such that an exposed underside of the screw head extends radially beyond the maximum radius of the screw shaft. The seating component comprises a screw channel comprising a planar screw seat having a minimum radius $R_3$ which is equal to or greater than $R_1$. The bottom end of the screw head comprises an annular contact surface for abutment against said screw seat, the contact surface being formed by the distal end of at least one downwardly extending protrusion on the underside of the screw head, wherein the annular contact surface has a minimum radius greater than the minimum radius of the screw seat.

In the present context the "bottom" of the screw component is considered to be the distal end of the screw shaft, i.e. the opposing end of the screw shaft to the screw head. The bottom end of the head is therefore the end of the head closest to the screw shaft and a downwardly extending protrusion is one that protrudes towards the bottom of the screw.

In accordance with conventional dental terminology, "apical" refers to the direction towards the bone and "coronal" to the direction towards the teeth. Therefore the apical part of a component is the part which, in use, is directed towards the jaw bone and the coronal part is that which is directed towards the oral cavity. When the screw component of the present invention is a dental screw component therefore, the bottom end of the screw head can also be considered as the apical end and the one or more protrusions as apically extending.

According to the present invention, the annular contact surface of the screw head is located at a radial location remote from the outer radius of the screw shaft. In other words, at the axial location of the annular contact surface a gap exists between the minimum radius of the contact surface and the radially inner part of the screw head. This is achieved by providing, on the underside of the screw head, one or more protrusions which extend in the downward direction to create the annular contact surface. The gap created between the inner portion of the screw head and the annular contact surface is great enough that the annular contact surface has a larger minimum radius than the minimum radius of the screw seat.

As the minimum radius of the contact surface is greater than the minimum radius of the screw seat, the innermost area of the screw seat will not be in contact with the screw head during use.

When tightening a screw only some of the applied torque is translated into pre-load. The overall torque which must be applied to the screw is significantly higher, as a large amount of torque is used to overcome the friction acting on the screw head and threads. In general it is estimated that only approximately 10-15% of the applied torque is used to tighten the screw.

In prior art screw systems the underside of the screw head is shaped to complement the screw seat. Therefore, when the screw seat is planar the underside of the screw is also planar. Thus, a large contact surface is formed. In effect, the entire underside of the screw head acts as an annular contact surface. In contrast, in the present invention, the at least one downwardly extending protrusion creates a smaller contact surface as only a part of the underside of the screw head forms the contact surface. The protrusion has the effect that not all of the radially overlapping areas of the screw head and screw seat are in contact with one another. As the annular contact surface has a minimum radius greater than the minimum radius of the screw seat, this has a larger friction radius than is achieved when using a traditional flat screw head, which also contacts the inner part of the screw seat. Consequently, the torque required to overcome the friction on the screw head is increased and hence reduces the percentage of torque translated into pre-loading force.

Therefore, a user who exceeds the recommended maximum torque limit is less likely to damage the screw as more of the applied torque is "absorbed" by the frictional resistance of the screw head.

In most systems, the minimum radius of the screw seat is equal to the maximum radius of the screw shaft, taking into account manufacturing tolerances. This provides the narrowest screw channel possible below the screw seat which can still accommodate the screw shaft. Consequently, traditional flat head screws comprise a planar underside that extends outwards from $R_1$.

Therefore, viewed from another aspect the present invention provides a screw component comprising a shaft extending along a longitudinal axis and having a maximum radius $R_1$, said shaft comprising a threaded section, said screw component further comprising, at one end of the screw shaft, a head, said head comprising a bottom end having a larger maximum radius $R_2$ than the screw shaft such that an exposed underside of the screw head extends radially beyond the maximum radius of the screw shaft, said bottom end comprising an annular contact surface for abutment against a planar screw seat, the contact surface being formed by the distal end of at least one downwardly extending protrusion on the underside of the screw, said contact surface having a minimum radius greater than the maximum radius of the screw shaft.

Preferred features of both aspects of the invention are described below.

The annular contact surface can be formed by a plurality of protrusions, such that the contact surface is discontinuous, or "broken". When the underside of the screw head comprises multiple protrusions, the distal ends of these may be at different radial locations. For example, the distance from the longitudinal axis to the protrusions may alternate from protrusion to protrusion. In such embodiments the minimum radius of the annular contact surface is set by the distal end of the protrusion(s) closest to the longitudinal axis.

However, preferably the distal ends of the plurality of protrusions are an equal distance from the longitudinal axis. In addition, although the protrusions may have differing shapes, it is preferred that these are identical, or at least that the shape of their distal ends are identical.

Preferably however the annular contact surface is formed by a single protrusion extending 360° about the longitudinal axis. Preferably this annular contact surface has a uniform inner radius, although it is possible for the annular contact surface to have an irregular, e.g. undulating, shape. Preferably the annular contact surface is uniform about the longitudinal axis, i.e. the minimum and maximum radii are both uniform. As the contact surface is intended to abut, in use, the planar screw seat, the annular contact surface lies in a plane perpendicular to the longitudinal axis.

The provision of a contact surface having a uniform inner radius enables the greatest friction radius to be achieved. The "friction radius" is the mean radius of the contact surface. This is the surface which in use contacts the screw seat and hence the greater this radius the greater the torque required to overcome the frictional resistance under the screw head.

Traditional methods of increasing the friction radius include widening the screw head and/or increasing the minimum radius of the screw seat. However, as discussed above, in certain systems, such as dental implant systems, where space is restricted, such increases are not possible or would lead to unacceptable weakening of the components clamped by the screw.

The present invention provides an alternative way of increasing the friction radius which does not require any loss of volume from the surrounding components. Instead, this can be achieved through a relatively minor modification to the underside of the screw head.

In principle it is preferable for the annular contact surface to be as narrow as possible and have a minimum radius that is as large as possible, in order to maximise the friction radius. For this reason it is also preferred that the maximum radius of the annular contact surface is equal to the maximum radius of the bottom end of the screw head. In a preferred embodiment the maximum radius of the annular contact surface is equal to the outer radius of the screw head. However, in practice manufacturing and other concerns must also be taken into account.

For example, the screw seat can be located at the end of the screw channel, such that the screw seat is formed on an exterior surface of the seating component. However, in many cases, the screw seat will be located within the screw channel. In such cases the screw channel is formed of at least two sections, a first section, having a first diameter, and a second section having a second, smaller diameter, wherein the screw seat is formed by the transition between these two diameters. In some components this transition may happen gradually, leading to a conical screw seat. However, this invention is only concerned with planar screw seats, where at least a part of the transition between the first and second diameters happens as a step change. At the transition between the wall of the first screw channel section and the screw seat a small radius is often formed, due to the manufacturing methods used to create this channel. When the screw head has an outer radius which is approximately equal to the diameter of the first screw channel section, an annular contact surface located at the radial edge of the screw head may not sit correctly on the screw seat and may further not be capable of smooth rotation.

In addition, depending on the function of the screw component, the head may taper radially outwards from the bottom end, such that the maximum radius of the screw head is significantly greater than the screw seat radius and hence the contact surface radius.

Therefore, alternatively the location of the contact surface can be defined in relation to the underside of the screw head or the minimum radius of the screw seat.

It is preferable for the annular contact surface to be located in the outer half of the underside of the screw head. More preferably the annular contact surface is located within the outer 75% of the underside of the screw head, and even more preferably in the outer 80%. In the context of the present invention the underside of the screw head is defined as the surface which extends radially beyond the outer boundary of the screw shaft to the maximum radius of the bottom end of the screw ($R_2-R_1$).

Preferably the minimum radius of the annular contact surface is at least 20% greater than the minimum radius of the screw seat, more preferably 25% greater. Preferably the contact surface is located within a range of 125-150% of the minimum radius of the screw seat. In a particularly preferred embodiment the contact surface is located within a range of 128-140% of the minimum radius of the screw seat.

Preferably, in use, at least the inner 50% of the surface area of the screw seat is not contacted by the annular contact surface.

The above ratios provide a suitable inner area of uncontacted screw seat in order to provide an effective increase in the friction radius, without requiring any increase in the overall diameter of the screw head or screw seat.

As discussed above, in many embodiments the minimum radius of the screw seat is approximately equal to the maximum radius of the screw shaft.

Consequently, in a preferred embodiment the minimum radius of the annular contact surface is at least 20% greater than the maximum radius of the screw shaft, more preferably 30% greater. Preferably the contact surface is located within a range of 125-150% of the maximum radius of the screw shaft. In a particularly preferred embodiment the contact surface is located within a range of 130-140% of the maximum radius of the screw shaft.

In the field of dental implants, in which the screw component has very small dimensions in order to fit within the implant, the maximum radius of the screw shaft, $R_1$, is preferably between 0.6 and 1 mm and the maximum radius of the bottom end of the screw head $R_2$ is preferably between 1.2 to 1.5 times $R_1$. A particularly preferred range for $R_2$ is 0.8-1.3 mm.

As mentioned above, it is desirable for the annular contact surface to be narrow, and therefore in some embodiments the distal end(s) of the protrusion(s) may be pointed or curved in shape. Upon tightening of the screw head against the screw seat, such a narrow contact surface would be deformed and flattened against the screw seat. This ensures a very close contact between the two surfaces and is particularly beneficial when the surface of the screw seat is rough or uneven. In many cases however it is preferable that the one or more protrusion comprises a flat distal end. This is easier to manufacture and reduces the risk of injury to the user. Preferably the contact surface has a radial width of 10-20% of the maximum screw shaft radius and/or 10-20% of the minimum screw seat radius.

In the field of dental implants, the contact surface has a width of preferably between 0.05-0.15 mm. Preferably the difference between the maximum radius of the screw shaft and the minimum radius of the annular contact surface is between 0.2 and 0.4 mm.

The at least one protrusion can be formed such that this extends downwardly at approximately right angles from the underside of the screw head. However, preferably the one or more protrusion is tapered at least on its radially inner side.

Such a taper brings a further advantage to the present invention. As the screw is tightened against the screw seat the tapered protrusion flexes slightly in the upward, or coronal, direction.

This is particularly beneficial in 3-part systems, such as when a separate screw component is used to attach a dental abutment to an implant. Over time and with use, it is common for the abutment to settle slightly into the implant. In prior art systems this results in the screw seat sinking away from the screw head and hence in a reduction in the friction between the components. This is evidenced by the removal torque necessary to unscrew the screw after use or dynamic testing, which is always significantly less than the initial insertion torque used.

It has been surprisingly found however, that in addition to increasing the maximum torque which can be withstood by the screw during insertion, the screw design of this preferred embodiment also increases the removal torque. This is considered to be due to the above mentioned flexing of the screw head. This enables the screw head to act as a spring and, as the abutment sinks during use, the screw head unflexes and lowers with the abutment such that a greater degree of contact is maintained between the screw seat and screw head. This therefore increases the removal torque required to unscrew the screw and thus increases the security of the connection.

Preferably the radially inner side of the one or more protrusion tapers downwards at an angle of between 15 and 25°, most preferably 20°. Preferably the taper is at least partially, preferably fully, curved over a radius. When the taper is only partially curved this curvature should preferably be located at the proximal end of the protrusion.

The axial location of the bottom end of the screw head is defined by the annular contact surface, which in accordance with the present invention is radially separated from the inner part of the screw head by a gap. The radially inner part of the bottom end of the screw head joins to the screw shaft. This part of the screw head can have a radius equal to $R_1$, or in some cases greater than $R_1$, as long as this is less than the minimum radius of the screw seat.

Preferably the screw comprises an undercut at the transition between the screw shaft and the screw head, such that the taper of the protrusion starts radially inwards of $R_1$. This enables the tapered protrusion to have a longer radial length, which in turn increases the spring effect. When the taper is curved over a radius this curve preferably continues into and forms at least a part of the undercut.

The undercut can be located within the screw shaft or screw head or both. In a preferred embodiment undercut is at least partially located in the screw shaft such that the upper end of the screw shaft has a radius less than $R_1$. This increases the tolerance between the screw shaft and the screw seat edge.

The provision of a tapered protrusion on the screw head is considered inventive in its own right and therefore, viewed from another aspect the present invention provides a fastening system comprising a screw component and a seating component. The screw component comprises a shaft extending along a longitudinal axis and having a maximum radius $R_1$, said shaft comprising a threaded section, said screw component further comprising, at one end of the screw shaft, a head, said head comprising a bottom end having a larger maximum radius $R_2$ than the screw shaft such that an exposed underside of the screw head extends radially beyond the maximum radius of the screw shaft. The seating component comprises a screw channel comprising a planar screw seat having a minimum radius $R_3$ equal to or greater than $R_1$. The bottom end of the screw head comprises an annular contact surface for abutment against this screw seat, the annular contact surface being formed by the distal end of at least one downwardly extending protrusion on the underside of the screw head, wherein said at least one downwardly extending protrusion is tapered at least on its radially inner side.

Preferably the minimum radius of the contact surface is greater than the minimum radius of the screw seat. The screw component in accordance with this aspect may additionally or alternatively have any or all of the preferred features discussed herein.

It has been found that, using a screw component in accordance with the present invention the maximum torque that can be withstood by the screw component can be increased up to 10%.

In accordance with the present invention therefore, the incidence rate of screw failure can be reduced without needing to make external dimensional or material alterations to the system. No alterations to the shape or volume of the clamped components, such as the implant and abutment, are required. Preferably the screw component is integrally formed.

The screw and seating components of the present invention can be used in any technological field in which standard flat head screws are used. The invention is particularly beneficial in systems in which there is limited ability to alter the external dimensions of the clamped components, such as dental implant systems. Therefore, preferably the screw component is a dental screw component. This can be, for example, a secondary dental component, such as a dental abutment, for direct attachment to a dental implant or other dental component. Preferably however the screw component is a dental screw arranged to attach one dental component, e.g. an abutment or other secondary component, to another, e.g. implant. The dental screw could also be used to attach, for example, a prosthesis to an abutment.

For the avoidance of doubt, a dental screw is an element which is used to clamp one component to another. It therefore can be seen as a "third component" of the system. The dental screw does not itself perform any function in the dental implant system other than to attach another component to the system via clamping. In contrast, when the screw component of the present invention is a secondary dental component, this performs an additional function once attached to the implant. For example, an abutment provides a support structure for the prosthesis while a healing cap seals the implant during osseointegration and assists in shaping the gingiva around the implant. A prosthesis provides a temporary or permanent replacement to a natural tooth or teeth.

In one preferred embodiment the screw component comprises a dental secondary component, such as an abutment and the seating component comprises a dental implant. In this embodiment the screw channel is formed by an interior bore in the implant. The planar screw seat may be formed within this bore or may be formed by the coronal end face of the implant, i.e. at the coronal end of the screw channel.

In another preferred embodiment the seating component comprises a dental secondary component and the screw component is a dental screw for securing the secondary component to an implant. In such embodiments the screw seat is usually located within the screw channel, which runs through the secondary component. The secondary component can be, for example, a dental abutment or an impression post.

BRIEF DESCRIPTION OF THE DRAWINGS

Preferred embodiments of the invention shall now be described, by way of example only, with reference to the accompanying drawings, in which.

DETAILED DESCRIPTION

Figure 1A:
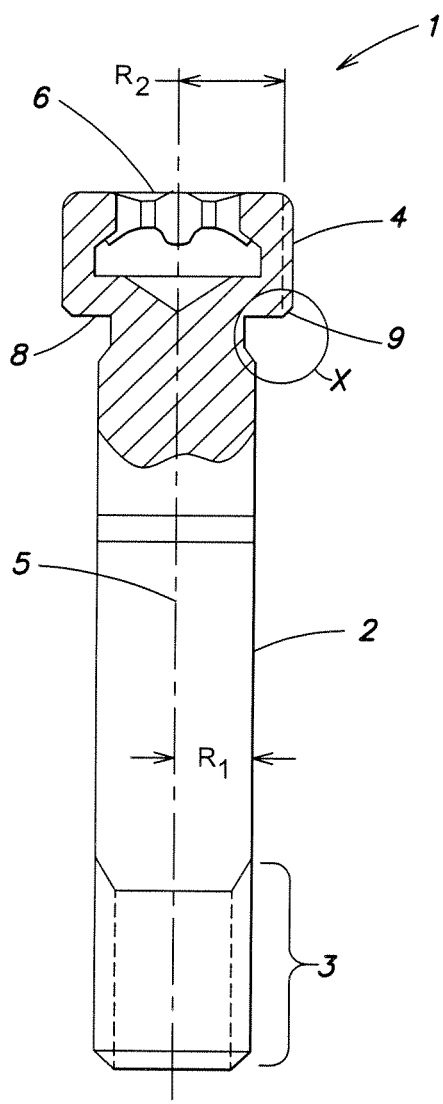
FIG. 1A shows a basal screw of the prior art.

FIGS. 1A and B show a basal screw 1 in accordance with prior art systems. It comprises a screw shaft 2 extending along a longitudinal axis 5. At its distal end the shaft 2 comprises a threaded section 3, the size and pitch of the thread being chosen for engagement with the internal threaded bore of an implant. At its opposing end shaft 2 joins to the screw head 4. Head 4 contains a hollow 6 in its coronal end which is shaped to allow insertion of a drive tool such as a screw driver. Hollow 6 has a non-circular symmetric outline such that torque can be transmitted from the drive tool to the screw 1.

The bottom, or apical, end of head 4 has a larger maximum radius $R_2$ than the maximum radius $R_1$ of the shaft 2. This results in an annular contact surface being formed by the underside 8 of the screw head 4. As the abutment or other component with which the screw engages must comprise a screw channel dimensioned to allow passage of the screw shaft 2 the maximum contact area possible between the screw head 4 and screw seat is $\pi(R_2^2 - R_1^2)$.

It is worth noting that the maximum radius $R_2$ of the bottom end is less than the overall maximum radius of the screw head 4. This is because a bevelled surface 9 links the bottom end to the outer circumference of the screw head 4. This improves the fit of the screw 1 within the screw channel, as will be demonstrated later.

Despite this bevel, underside 8 provides a relatively large surface area with which the head 4 can contact the screw seat of the abutment or other secondary component. Further, this surface area extends from the maximum radius $R_1$ of the screw shaft 2 outwards.

Figure 1B:
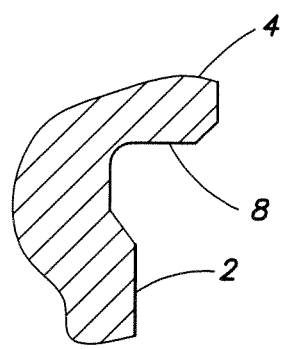
FIG. 1B shows a detail X from FIG. 1A
Figure 2A:
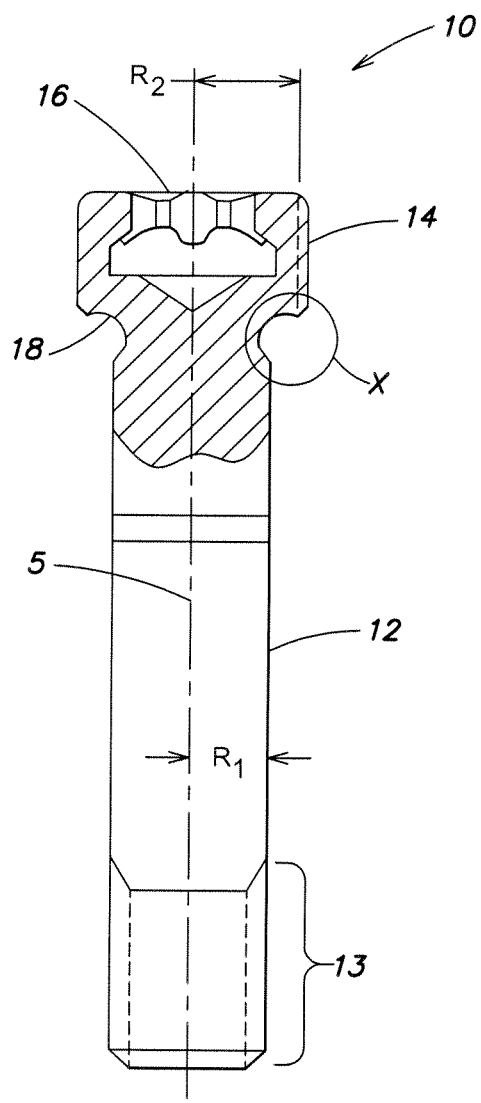
FIG. 2A shows a basal screw in accordance with the present invention.

FIG. 2A shows a screw 10 in accordance with the present invention. The screw shaft 12 is identical to that of the prior art screw shown in FIG. 1 and comprises a threaded section 13 at its distal end and joins to a screw head 14 at the opposite end. Once again, head 14 comprises a hollow 16 shaped to allow engagement with a drive tool. Although shown at the distal end threaded section 13 could alternatively be positioned at a different axial location on the shaft 2.

In contrast to the prior art, the underside 18 of screw head 14 is not planar but instead comprises a downwardly extending protrusion 17. This protrusion 17 tapers downwards to a flat distal surface, which defines the bottom, or apical, end 15 of the screw head 14. The taper is formed on the radially outer side by bevelled surface 19 and on the radially inner side by a concave surface.

The shape of the underside 18 results in the creation of an annular contact surface having a width less than $R_2 - R_1$ and which is located towards the outer radius of the screw head 14. This shape of screw head increases the friction radius of the screw and hence increases the torque required in order to overcome the frictional resistance of the screw head.

Figure 3A:
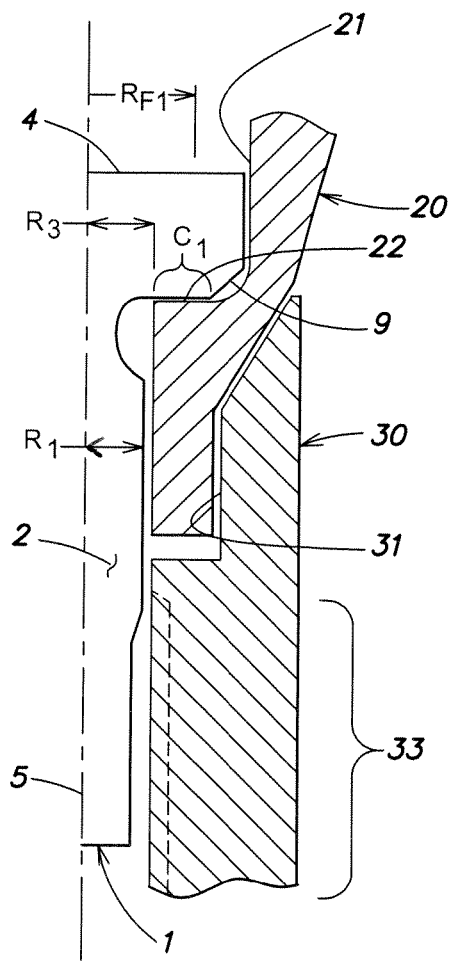
FIG. 3A shows a schematic representation of the screw of FIG. 1 in contact with the screw seat of a secondary component.

This is demonstrated with reference to FIGS. 3A and B. FIG. 3A shows schematic view of a partial cross section of the screw 1 of FIG. 1 within a 3-part implant system. Abutment 20 comprises a screw channel 21 having a coronal part and an apical part, separated by a step change in diameter which forms screw seat 22. Screw seat 22 is planar and perpendicular to the longitudinal axis 5 of the system. Due to manufacturing methods the transition from the outer wall of the coronal part of the screw channel 21 to the seat 22 is curved.

Abutment 20 is seated in an internal bore 31 of implant 30. The bore is shaped to snugly accommodate the abutment 20 and comprises a threaded section 33.

In order to connect the abutment 20 to the implant 30 screw 1 is passed through screw channel 21 until the threaded section 3 of the screw 1 can engage with the threaded section 33 of the implant. By tightening screw 1 the head 4 is forced down onto the screw seat 22 and clamps the abutment 20 within the implant 30.

The bevelled edge 9 of screw head 4 prevents any interference with the curved transition area of the screw channel 21. The planar surface of the underside 8 creates a broad contact region $C_1$ between the screw head 4 and screw seat 22. The friction radius of the system shown in FIG. 3A is the mean radius of this contact region $R_{F1}$.

When torque is applied to the screw 1 via the hollow 6 (not shown in FIG. 3A) a part of this torque will be used to overcome the frictional resistance under the screw head 4, another part will be used overcoming the frictional resistance of the screw threads and the remainder will tighten the screw and increase the tension in the screw body. Too much applied torque will over tension the screw 1 and cause this to fracture and break.

Figure 3B:
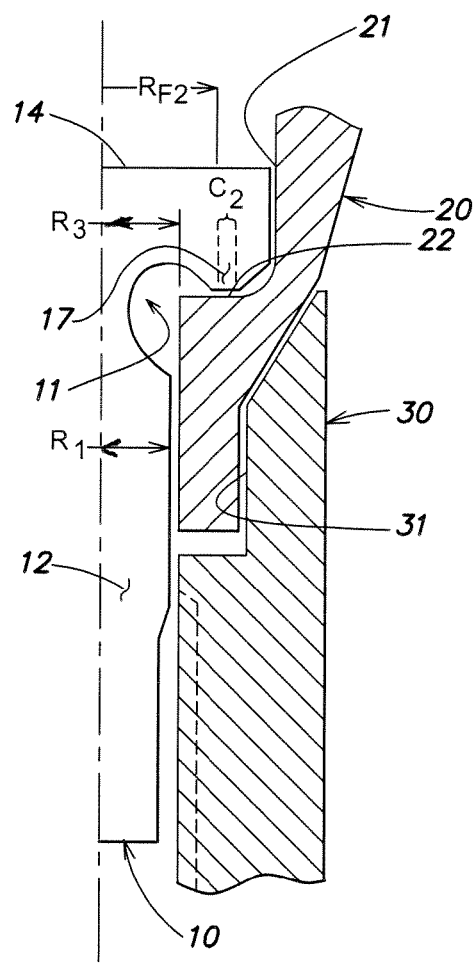
FIG. 3B shows a schematic representation of the screw of FIG. 2 in contact with the same screw seat.

FIG. 3B shows the same implant system as FIG. 3A, however this time screw 10 is used to connect the abutment 20 to the implant 30. As can be seen, the downwardly extending protrusion 17 significantly reduces the contact region $C_2$ between the screw head 14 and the screw seat 22.

Significantly, no contact between the surfaces exists at the radially innermost area of the screw seat 22 because the contact surface of the screw head has a greater minimum radius than the minimum radius $R_3$ of the screw seat 22. This radius is similar to that of the maximum radius $R_1$ of the screw shaft 12, as the screw shaft 12 must be able to pass through the screw seat 22 into the apical part of the screw channel 21.

The lack of contact at the radially inner area of the screw seat 22 increases the friction radius $R_{F2}$ of the system and consequently the torque needed to overcome the frictional resistance under the screw head 14. By using a screw in accordance with the present invention therefore a smaller percentage of the applied torque will be used to tension the screw body and hence the screw 10 can withstand more torque before over tensioning occurs.

Protrusion 17 is located as close to the outer radial edge of the screw head 14 as possible, in order to increase the friction radius $R_{F2}$. In addition the distal surface of protrusion 17 is made as narrow as possible.

Figure 2B:
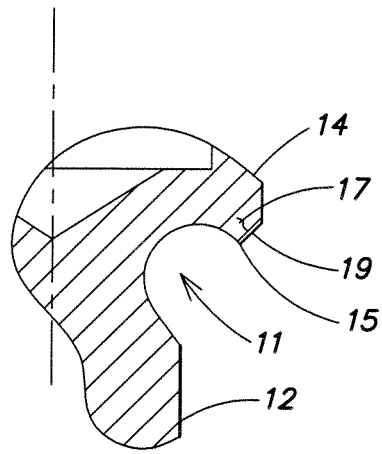
FIG. 2B shows a detail X from FIG. 2A.

The protrusion 17 of the screw 10, shown in FIGS. 2 and 3B has a tapered surface on its radially inner side. This has an additional benefit as it allows the screw head 14 to flex. As the screw head 14 is drawn downwards onto the screw seat 22, the tapered surface enables the protrusion to pivot slightly. The screw head 14 thus acts as a loaded spring.

During use of the abutment 20, this settles or sinks further into the implant bore 31. In prior art systems this lessens the torque required to remove the screw 1. Using a screw according to a preferred embodiment of the present invention however, as the abutment 20 settles lower in the implant 30 the tapered protrusion 17 unflexes and hence maintains a better contact with the screw seat. This leads to a higher removal torque even after prolonged use of the abutment 20.

In order to increase the length of this taper, the screw 10 comprises an undercut 11 at the transition from the screw shaft 12 to the screw head 14. This increases the spring effect of the protrusion 17 and in addition increases the tolerance between the screw head 14 and screw seat 22. In this embodiment it is the curve of the taper which continues into and forms a part of the undercut 11.

Comparative tests have been run on screws having the designs shown in FIG. 1 and FIG. 2. It was found that the average breakage torque was increased from 51.8 Ncm, in the case of screw 1, to 57.8 Ncm in the case of screw 10. In addition, after fatigue testing with a load of 280 N, the removal torque of screw 10 was 26.1 Ncm compared with 17.9 Ncm in respect of screw 1.

Figure 6:
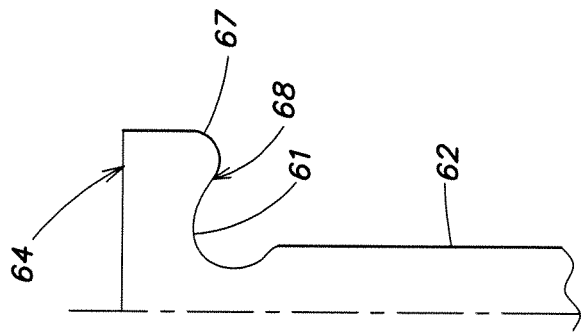
FIGS. 4-6 show alternative seat head designs according to the present invention.
Figure 5:
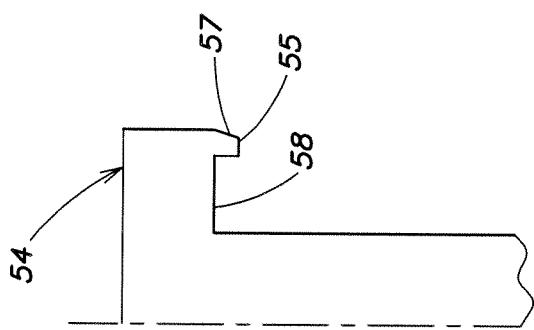
Figure 4:
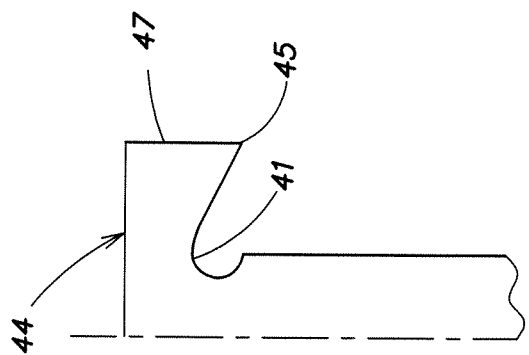

FIGS. 4-6 show some further embodiments of the present invention. FIG. 4 shows a screw head 44 having a tapered protrusion 47 that tapers to an end point which forms the apical end 45 of the head 44, located at the outer radius of the screw head. This screw 40 provides the optimum friction radius possible for a screw of a given outer radius and can be used in situations in which manufacturing tolerances permit, for example, when the screw seat 22 is formed by the outer surface of the seating component and/or extends radially beyond the screw head. This embodiment features an undercut 41 which increases the spring effect of the tapered protrusion 47. This undercut 41 is located in the screw head 44.

FIG. 5 shows an alternative screw head 54 in which protrusion 57 extends at right angles from the underside 58 of the head 54. Providing a flat apical end 55 and contact surface enables better consistency and predictability of the screw. In this embodiment no undercut is present at the transition between the shaft and head.

FIG. 6 shows a screw head 64 having an undulating underside 68 that results in a curved protrusion 67. Here, the undercut 61 extends into both the screw shaft 62 and screw head 64.

Figure 7:
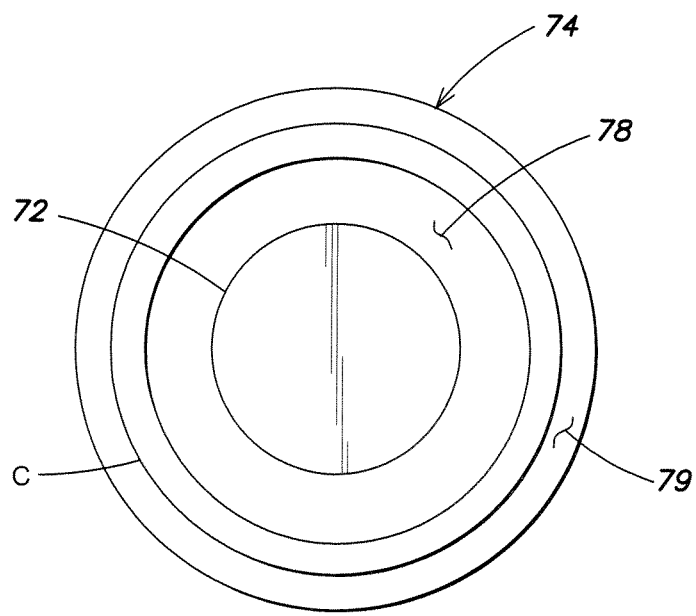
FIG. 7 shows a base view of a screw component in accordance with the present invention.

FIG. 7 shows a generalised bottom view of a screw according to the present invention. Screw head 74 has a greater radius than screw shaft 72 and so extends outwards from this forming an underside 78. Bevelled surface 79 extends between the radial edge of the underside 78 and the circumferential edge of screw head 74. The underside 78 of the screw head 74 comprises a protrusion which extends in the apical direction to a distal end surface which forms a continuous annular contact surface C. The location, width and shape of the protrusion can vary, as shown in FIGS. 2 and 4-6. In FIG. 7 a single protrusion extends 360° about the longitudinal axis of the screw to form a uniform, continuous contact surface.

Figure 8:
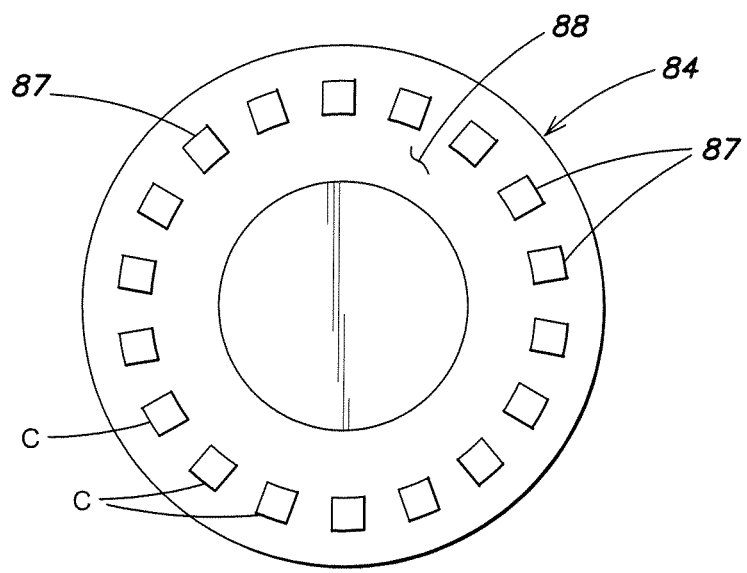
FIG. 8 shows a base view of a screw components in accordance with another embodiment of the present invention.

It is also possible for the contact surface to be formed by a plurality of protrusions. This is shown in FIG. 8. Here it can be seen that the underside 88 of the screw head 84 comprises multiple protrusions 87, which again can have any of the shapes shown in previous embodiments, each extending apically to a distal surface, these distal surfaces in combination forming a broken or discontinuous annular contact surface C.

The invention has mainly been described above in relation to a separate screw component, which can be used to connect a secondary component such as an abutment to an implant. However, it is also possible for the secondary component itself to form the screw component of the present invention. When it is not necessary to know with certainty the exact angular position of the component with respect to the implant the secondary component is often directly screwed into the implant. This direct connection is common for example, when the implant is intended for supporting a bridge, i.e. a single prosthesis which replaces multiple teeth. In such situations the bridge is attached to two or more implants and the angular orientation of the bridge is thus defined by these multiple connection points. Other secondary components, such as healing caps, which are only used on a temporary basis and do not support a prosthesis, may also be directly screwed to the implant.

Figure 9:
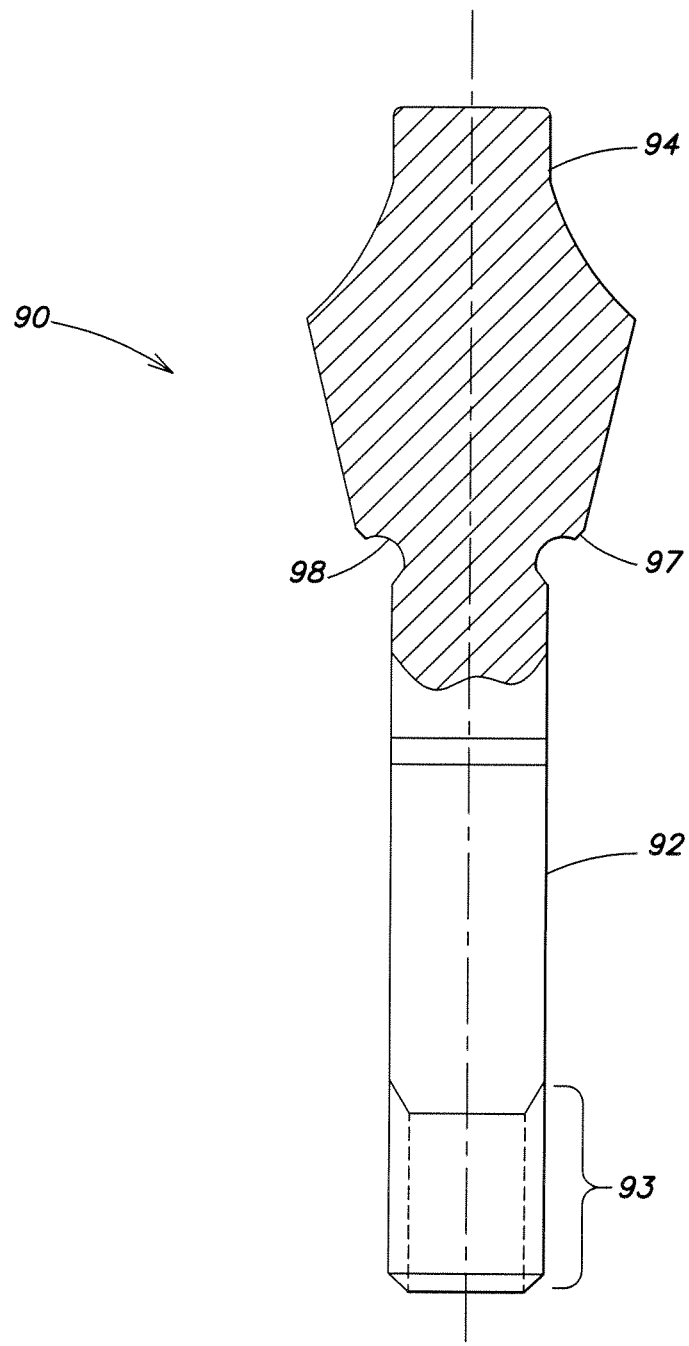
FIG. 9 shows an abutment in accordance with the present invention.

FIG. 9 shows a secondary component designed for direct connection to an implant. The component 90 comprises shaft 92 having a threaded section 93 for threaded connection to the implant. The component 90 further comprises a head 94, which in use protrudes from the implant into and/or through the soft tissue.

The bottom or apical end the head 94 has a larger radius than the shaft 92, such that an underside 98 is created. The underside 98 comprises an apically extending protrusion 97 which extends 360° about the longitudinal axis of the component such that an annular contact surface is formed. The detail circled in FIG. 9 is very similar in configuration to the screw 10 shown in FIG. 2A. The annular contact surface of component 90 has a larger minimum radius than the maximum radius of the shaft 92 and the minimum radius of the screw seat of the implant. Therefore, the friction radius of the screw head is increased in relation to prior art components.

The above described embodiments are for illustrative purposes only and the skilled man will realize that many alternative arrangements are possible which fall within the scope of the claims.

Where technical features mentioned in any claim are followed by reference signs, those reference signs have been included just for the sole purpose of increasing intelligibility of the claims and accordingly, such reference signs do not have any limiting effect on the scope of each element identified by way of example by such reference signs.

The invention claimed is:

1. A fastening system comprising a screw component and a seating component,
  the screw component comprising
    a shaft extending along a longitudinal axis and having a maximum radius $R_1$, said shaft comprising a threaded section,
    said screw component further comprising, at one end of the screw shaft, a head,
    the head comprising a bottom end having a larger maximum radius $R_2$ than the screw shaft such that an exposed underside of the screw head extends radially beyond the maximum radius of the screw shaft,
  the seating component comprising
    a screw channel comprising a planar screw seat having a minimum radius $R_3$, which is equal to or greater than $R_1$,
    the bottom end of the screw head comprising an annular contact surface (C) for abutment against said screw seat, said contact surface being formed by a distal end of at least one downwardly extending protrusion on the underside of the screw head, the annular contact surface having a minimum radius greater than the minimum radius of the screw seat, such that, in use, an innermost area of the screw seat is not in contact with the screw head, wherein a radially inner side of the at least one downwardly extending protrusion is tapered and the screw component comprises an undercut at a transition between the screw shaft and the screw head, the undercut being radially inward of $R_1$, and continuing radially outwardly to the taper of the radially inner side of the protrusion.

2. A fastening system as claimed in claim 1, wherein the annular contact surface (C) is formed by the distal end of a single protrusion extending 360° about the longitudinal axis.

3. A fastening system as claimed in claim 1, wherein the annular contact surface (C) has a uniform inner radius.

4. A fastening system as claimed in claim 1, wherein the annular contact surface (C) is located in an outer half of the underside of the screw head.

5. A fastening system as claimed in claim 1, wherein the minimum radius of the annular contact surface (C) is at least 25% greater than the minimum radius $R_3$ of the screw seat.

6. A fastening system as claimed in claim 5, wherein the contact surface (C) is located within a range of 128-140% of the minimum radius $R_3$ of the screw seat.

7. A fastening system as claimed in claim 1, wherein minimum radius of the annular contact surface (C) is at least 30% greater than the maximum radius $R_1$ of the screw shaft.

8. A fastening system as claimed in claim 1, wherein the distal end comprises a flat distal end.

9. A fastening system as claimed in claim 1, wherein the radially inner side tapers downwards towards the seating component at an angle of between 15 and 25°.

10. A fastening system as claimed in claim 9, wherein the taper is at least partially curved over a radius.

11. A fastening system as claimed in claim 10, wherein the curve of the taper continues into and forms at least part of the undercut.

12. A fastening system as claimed in claim 9, wherein the angle is 20°.

13. A fastening system as claimed in claim 1, wherein the screw component is a dental screw for attaching an abutment or other secondary component to a dental implant.

* * * * *